(12) United States Patent
Yabuhara

(10) Patent No.: US 9,831,636 B2
(45) Date of Patent: Nov. 28, 2017

(54) SEMICONDUCTOR LASER DEVICE

(71) Applicant: Kabushiki Kaisha Toshiba, Minato-ku (JP)

(72) Inventor: Hidehiko Yabuhara, Kamakura (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/123,255

(22) PCT Filed: Sep. 4, 2014

(86) PCT No.: PCT/JP2014/073371
§ 371 (c)(1),
(2) Date: Sep. 2, 2016

(87) PCT Pub. No.: WO2015/136739
PCT Pub. Date: Sep. 17, 2015

(65) Prior Publication Data
US 2017/0063042 A1 Mar. 2, 2017

(30) Foreign Application Priority Data
Mar. 13, 2014 (JP) .................. 2014-050377

(51) Int. Cl.
*H01S 5/34* (2006.01)
*H01S 5/227* (2006.01)
*G01N 21/3504* (2014.01)

(52) U.S. Cl.
CPC ............ *H01S 5/3402* (2013.01); *H01S 5/227* (2013.01); *H01S 5/3408* (2013.01); *G01N 21/3504* (2013.01)

(58) Field of Classification Search
CPC ....... H01S 5/3402; H01S 5/227; H01S 5/3408
See application file for complete search history.

(56) References Cited

U.S. PATENT DOCUMENTS 6,091,751 A 7/2000 Berger
2008/0273565 A1 11/2008 Gmachl et al.
(Continued)

FOREIGN PATENT DOCUMENTS

JP 10-261844 A 9/1998
JP 2008-177366 A 7/2008
(Continued)

OTHER PUBLICATIONS

Gmachl et al. (Quantum cascade lasers with a heterogeneous cascade: Two and multiple wavelength operation, Proceedinds of SPIE, 2002, vol. 4651, pp. 286-293).*
(Continued)

*Primary Examiner* — Dung Nguyen
(74) *Attorney, Agent, or Firm* — Oblon, McClelland, Maier & Neustadt, L.L.P.

(57) ABSTRACT

According to one embodiment of the invention, a semiconductor laser device includes a plurality of first unit stacked bodies and a plurality of second stacked bodies. The plurality of first unit stacked bodies have an emission region including a first quantum well layer and capable of emitting a first infrared light by an intersubband transition, and an electron injection region capable of transporting an electron relaxed to a mini-band level in the emission region to a downstream unit stacked body. The plurality of second unit stacked bodies have an emission region including a second quantum well layer and capable of emitting a second infrared light by an intersubband transition, and an electron injection region capable of transporting an electron relaxed to a mini-band level in the emission region of the second quantum well layer to a downstream unit stacked body. The second quantum well layer has at least one well width different from a well width of the first quantum well layer.

(Continued)

The first unit stacked body and the second stacked body are stacked with spatial periodicity.

10 Claims, 6 Drawing Sheets

(56) References Cited

U.S. PATENT DOCUMENTS

| | | | |
|---|---|---|---|
| 2010/0111127 A1* | 5/2010 | Edamura | B82Y 20/00 372/45.012 |
| 2013/0148678 A1 | 6/2013 | Diehl et al. | |

FOREIGN PATENT DOCUMENTS

| | | | |
|---|---|---|---|
| JP | 2010-278326 | * | 12/2010 |
| JP | 2010-278326 A | | 12/2010 |

OTHER PUBLICATIONS

English translation of International Search Report dated Dec. 2, 2014 in PCT/JP2014/073371.

English translation of Written Opinion dated Dec. 2, 2014 in PCT/JP2014/073371.

Combined Taiwanese Office Action and Search Report dated Jul. 11, 2016 in Patent Application No. 103131036 (with English language translation).

Claire Gmachl, et al., "Quantum cascade lasers with a heterogeneous cascade: Two- and multiple-wavelength operation" Proceedings of SPIE, vol. 4651, 2002, pp. 286-293.

Axel Straub, et al., "Two-wavelength quantum cascade lasers with heterogeneous cascades" IEEE Conference on Optoelectronic and Microelectronic Materials and Devices, 2002, pp. 141-144.

* cited by examiner

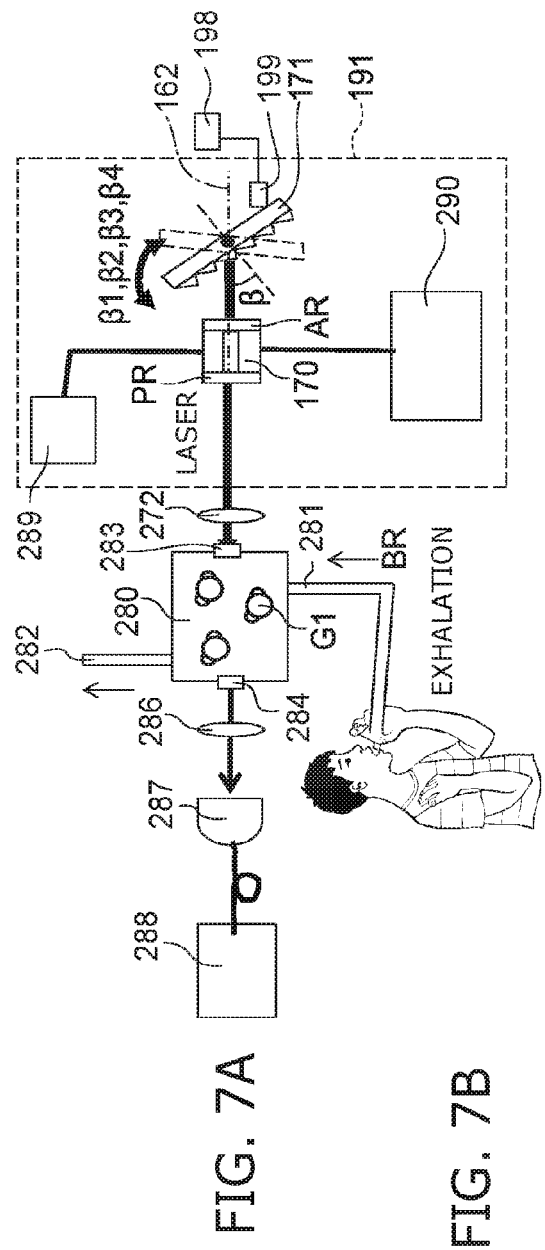
FIG. 7A
FIG. 7B
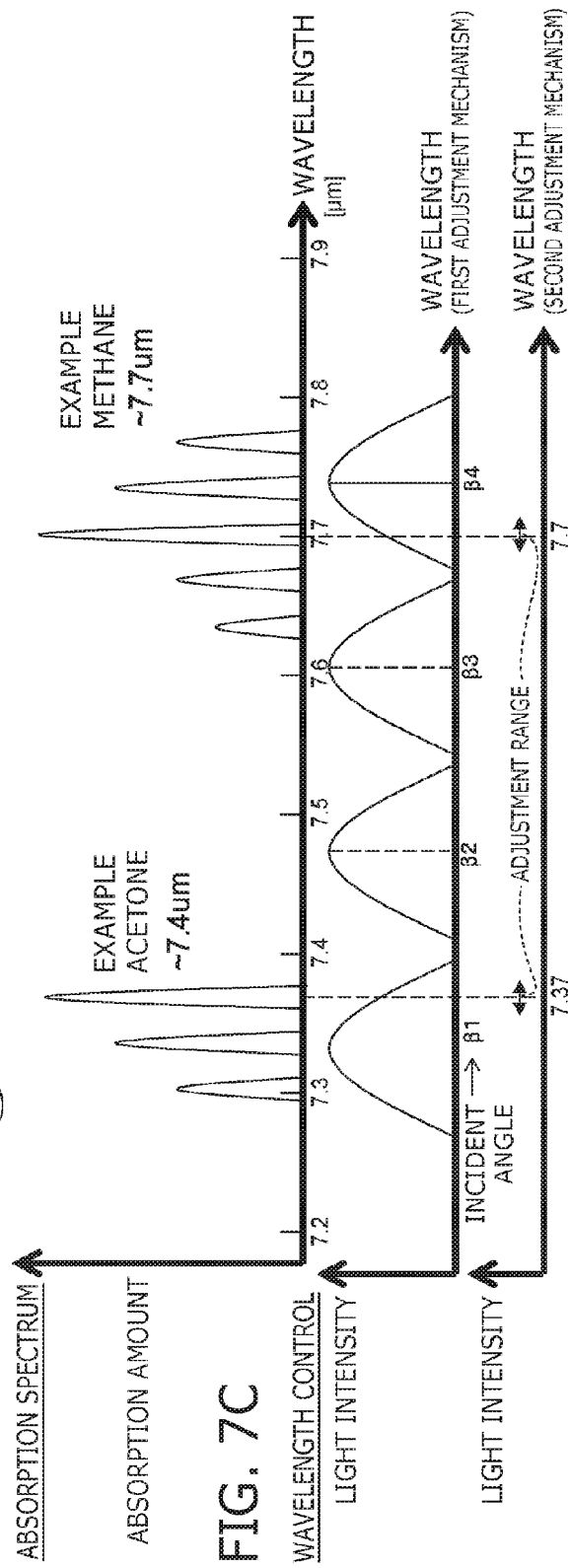
FIG. 7C

SEMICONDUCTOR LASER DEVICE

TECHNICAL FIELD

This invention relates to a semiconductor laser device.

BACKGROUND ART

Laser devices emitting infrared light are applied to a broad range of fields such as environment measurement. A quantum cascade laser made of a semiconductor is small in size and has high convenience, and enables high precision measurement.

The quantum cascade laser includes an active layer alternately stacked with, for example, GaInAs and AlInAs, and including a quantum well layer. The quantum cascade laser has a structure where both side surfaces of the active layer are interposed between, for example, InP cladding layers. In this case, the cascade-connected quantum well layer is capable of emitting infrared laser light with a wavelength of 4 to 20 μm by intersubband transition of a carrier.

Various gases included in air have an absorption spectrum peculiar to the gas due to infrared ray radiation. For this reason, type and concentration of the gas can be known by measuring an infrared ray absorption amount. In this case, a wavelength range of the laser light emitted from the quantum cascade laser is required to be wide.

PRIOR ART DOCUMENT

Patent Document

[Patent Document 1] JP 2010-278326 A (Kokai)

SUMMARY OF INVENTION

Problem to be Solved by Invention

The embodiments of the invention provide a semiconductor laser device capable of emitting infrared light in a wide wavelength band.

Means for Solving Problem

According to one embodiment of the invention, a semiconductor laser device includes a plurality of first unit stacked bodies and a plurality of second unit stacked bodies. The plurality of first unit stacked bodies have an emission region including a first quantum well layer and capable of emitting a first infrared light by an intersubband transition, and an electron injection region capable of transporting an electron relaxed to a mini-band level in the emission region to a downstream unit stacked body. The plurality of second unit stacked bodies have an emission region including a second quantum well layer and capable of emitting a second infrared light by an intersubband transition, and an electron injection region capable of transporting an electron relaxed to a mini-band level in the emission region of the second quantum well layer to a downstream unit stacked body. The second quantum well layer has at least one well width different from a well width of the first quantum well layer. The first unit stacked body and the second unit stacked body are stacked with spatial periodicity.

BRIEF DESCRIPTION OF DRAWINGS

FIG. 7A is a configuration view of an exhalation diagnosis device according to the embodiment, FIG. 7B a schematic view of an absorption spectrum of a plurality of gases, FIG. 7C is a view for describing a first adjustment mechanism and a second adjustment mechanism of a wavelength control unit.

EMBODIMENTS OF INVENTION

Embodiments of the invention will be described hereinafter with reference to the accompanying drawings.

Figure 1A:
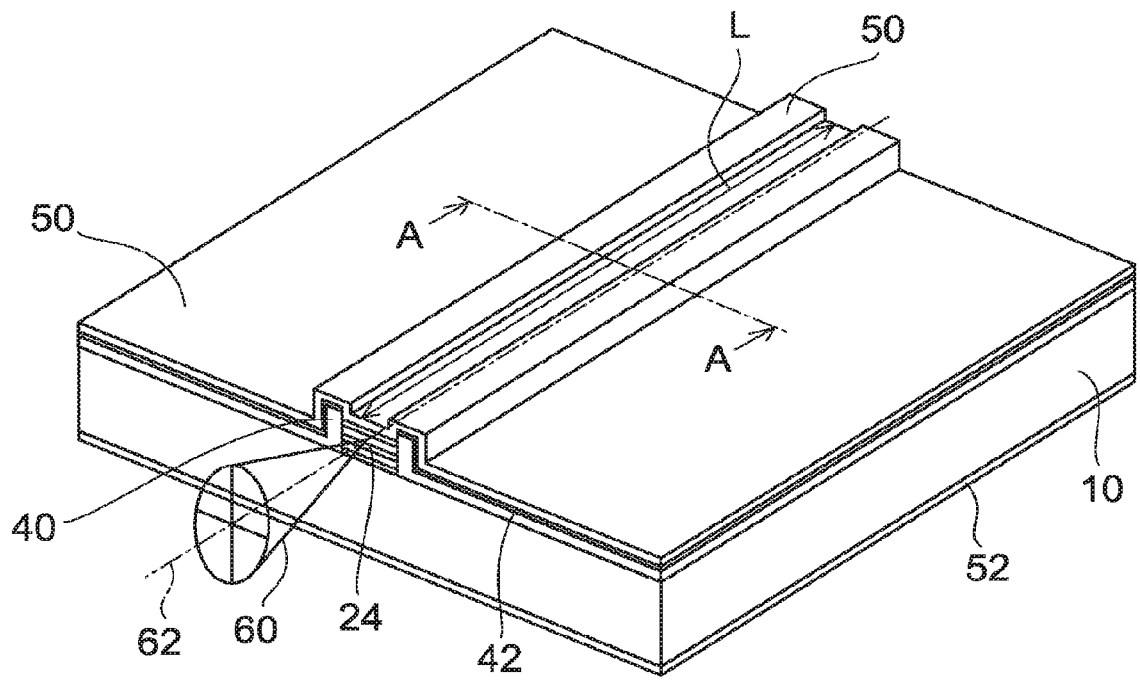
FIG. 1A is a schematic perspective view a partially cut semiconductor laser device according to a first embodiment of the invention.
Figure 1B:
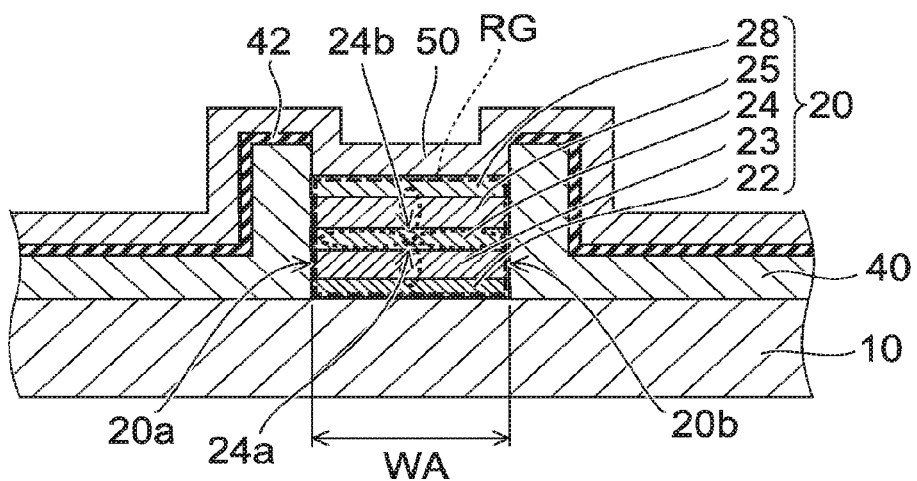
FIG. 1B is a schematic cross-sectional view along A-A line.

FIG. 1A is a schematic perspective view a partially cut semiconductor laser device according to a first embodiment of the invention, FIG. 1B is a schematic cross-sectional view along A-A line.

The semiconductor laser device includes at least a substrate 10, a stacked body 20 provided on the substrate 10, and a dielectric layer 40. In FIG. 1A, a first electrode 50, a second electrode 52 and an insulating film 42 are further included.

The stacked body 20 includes a first cladding layer 22, a first guide layer 23, an active layer 24, a second guide layer 25, and a second cladding layer 28. Each of a refractive index of the first cladding layer 22 and a refractive index of the second cladding layer 28 is set to be lower any of refractive indices of the first guide layer 23, the active layer 24 and the second guide layer 25, and an infrared laser light 60 is set to be adequately confined in a stacking direction of the active layer 24.

The stacked body 20 has a striped configuration, and can be called a ridge waveguide RG. If two end surfaces of the ridge waveguide RG are assumed to be mirror surface, stimulated emission light is emitted from a light emission surface as the infrared laser light 62. In this case, an optical axis 62 is defined as a line which connects a center of a cross section of an optical resonator having a mirror surface as a resonant surface. That is, the optical axis 62 coincides with an extending direction of the ridge waveguide RG.

If a width WA in a direction parallel to a first surface 24a and a second surface 24b of the active layer 24 is too wide in a cross section perpendicular to the optical axis 62, a high-order mode is generated in a horizontal transverse direction, and a high output becomes difficult. If the width WA of the active layer 24 is, for example, 5 to 20 μm or the like, the horizontal transverse mode is easily controlled. If a refractive index of the dielectric layer 40 is lower than a refractive index of any layer constituting the active layer 24, the ridge waveguide RG can be constituted along the optical axis 62 by the dielectric layer 40 provided so as to interpose side surfaces 20a, 20b of the stacked body 20.

Figure 2:
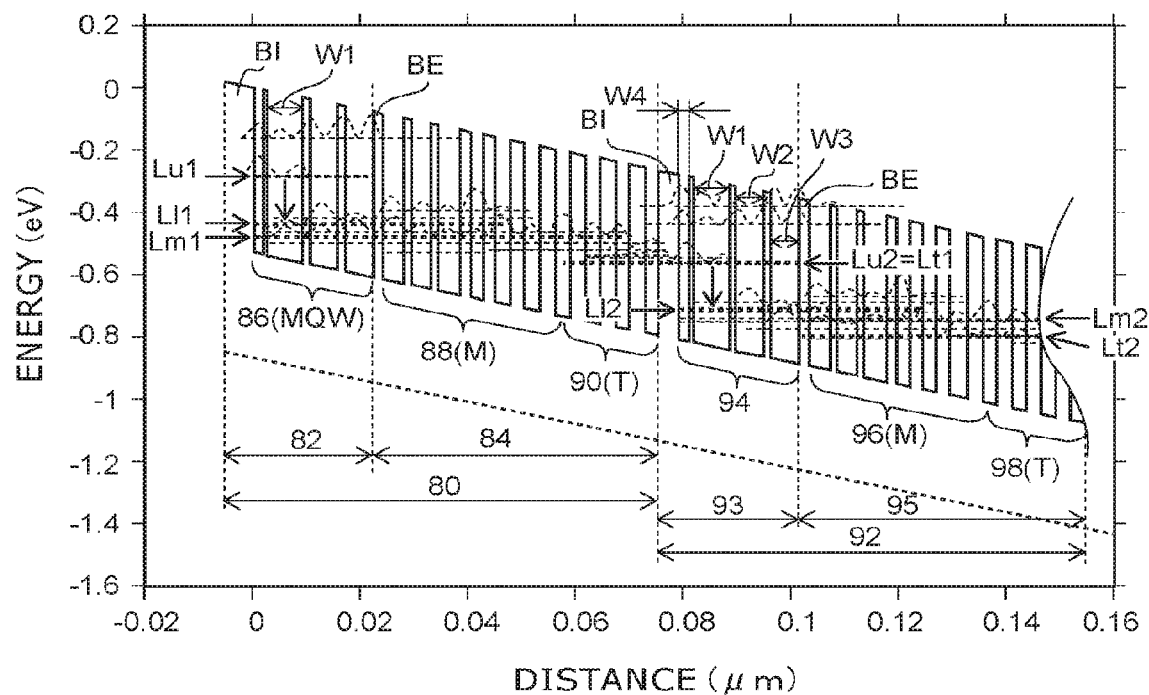
FIG. 2 is an energy band diagram describing the operation of the semiconductor laser device according to the first embodiment.

FIG. 2 is an energy band diagram describing the operation of the semiconductor laser device according to the first embodiment.

The active layer 24 has a cascade structure where an emission region and an injection region are alternately stacked. Such a semiconductor laser can be called a quantum cascade laser. A first unit stacked body 80 includes a first emission region 82 and a first injection region 84. The first injection region 84 includes an electron injection region 88 and an extraction barrier layer BE. The first injection region 84 may further include an adjustment quantum well layer 90 on a downstream. The first emission region 82 is capable of emitting a first infrared laser light by an intersubband transition of a first quantum well layer 86. A carrier (electron in the figure) is injected from the first injection region 84 into a second emission region 94, after the intersubband transition, the electron is extracted from the second emission region 94 into a second injection region 96. The carrier moves from the upstream to the downstream. That is, the first unit stacked body 80 is located on the upstream. On the other hand, a second unit stacked body 92 is located on the downstream. For example, it can be said that the first injection region 84 transports (inject) the carrier (electron) to the second emission region 93 of the second unit stacked body 92.

The second unit stacked body 92 includes the second emission region 93 and a second injection region 95. The second injection region 95 includes an electron injection region 96 and an extraction barrier layer BE. The second injection region 95 may further include an adjustment quantum well layer 98 on the downstream. The second emission region 93 is capable of emitting a second infrared light including the infrared laser light by an intersubband transition of a second quantum well layer 94. The second injection region 95 is capable of relaxing energy of a carrier (electron in the figure) injected from the second emission region 93 to a mini-band level Lm2.

In the first quantum well layer 86 and the second quantum well layer 94, when the well width W1 is narrowed to, for example, 10 nm or less, energy levels are discrete and a subband (high level Lu) and a subband (low level Ll) or the like are produced. The carrier such as an electron injected from an injection barrier layer BI can be effectively confined in the quantum well layer. For this reason, in the case where the carrier transits from the high level Lu to the low level Ll, a photon (hv) corresponding to energy differences (Lu1−Ll1), (Lu2−Ll2) or the like is emitted (transition of carrier such as electron).

The intersubband transition occurs in one of a conduction band or a valence band. That is, recombination of a hole and an electron due to a pn junction is not necessary and light is emitted by transition of only one of the carriers. In the case of the figure, in the semiconductor stacked body, an electron 70 is injected into a quantum well layer via the injection barrier layer BI by a voltage applied between the first electrode 50 and the second electrode 52, and the intersubband transition occurs.

The unit stacked body has a plurality of mini-bands (also referred to as subband). It is favorable that energy difference in the mini-band is small and the mini-band is close to a continuous energy band. The electron at the low level Ll1 of the first emission region 86 is relaxed to a mini-band level Lm1, passes through the extraction barrier layer BE, is injected into the first injection region 88, and is transferred (injected) into the downstream unit stacked body. The electron at the low level Ll2 of the second emission region 93 is relaxed to the mini-band level Lm2, passes through the extraction barrier layer BE, is injected into the second injection region 95, and is transferred (injected) into the downstream unit stacked body.

A well layer determining the intersubband transition of the quantum well layers in the emission region is referred to as a first well layer, and the width is expressed by W1. In the first embodiment, the well layer width W1 generating the electron transition accompanying with light emission in the second quantum well layer 94 is different from the well layer width W1 generating the electron transition accompanying with light emission in the first quantum well layer 86.

Figure 3:
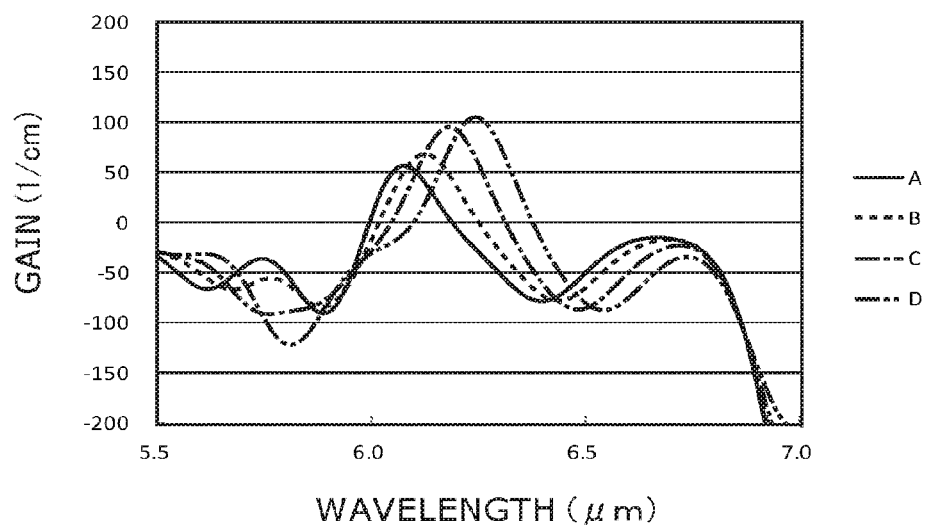
FIG. 3 shows a graph of a gain to an emission wavelength when changing a width of a first well layer.

FIG. 3 shows a graph of a gain to an emission wavelength when changing the width of the first well layer.

The vertical axis represents a gain (1/cm), and the horizontal axis represents an emission wavelength (μm).

In response to increasing the width W1 of the first well layer to 6.3 nm (A), 6.4 nm (B), 6.5 nm (C), 6.6 nm (D), the peak of the emission wavelength becomes long to 6.1 μm, 6.15 μm, 6.2 μm, 6.25 μm. The peak of the emission wavelength can be changed by changing the width W1 of the first well layer of the unit stacked body.

In the first embodiment, the first unit stacked body 80 and the second unit stacked body 92 are stacked with spatial periodicity. Therefore, a quantum cascade laser including a plurality of unit stacked bodies having different width W1 of the first well layer and having a wide emission wavelength band can be achieved.

The first unit stacked body 80 and the second unit stacked body 92 can be alternately stacked. Otherwise, three types of unit stacked bodies may be stacked periodically like A-B-C-A-B-C . . . . Furthermore, A-A-B-A-A-B . . . may be accepted. The stacked number can be, for example, 20 to 50 or the like.

In the first embodiment, the substrate 10 can be based on InP or the like. The first cladding layer 22 and the second cladding layer 28 can be based on InP or the like. The first guide layer 23 and the second guide layer 25 can be based on InGaAs or the like. The active layer 24 can be based on InGaAs ($In_{0.53}Ga_{0.47}As$ or the like)/$In_{0.52}Al_{0.48}As$ or the like.

The first cladding layer 22 and the second cladding layer 28 can have, for example, an n-type impurity concentration of $6 \times 10^{18}$ cm$^{-3}$ by Si doping, and the thickness can be, for example, 1 μm. The first guide layer 23 and the second guide layer 25 can have, for example, an n-type impurity concentration of $4 \times 10^{16}$ cm$^{-3}$ by Si doping, and the thickness can be, for example, 3.5 μm. A part of the quantum well layer forming the injection region may be doped with Si.

(Table 1) shows an example of a unit stacked body structure constituting a quantum cascade laser according to a second embodiment.

TABLE 1

Film Thickness: Unit nm

|  |  | Comparative example (structure A) | I (structure B + adjustment layer 1) | II (structure C + adjustment layer 2) | III(structure C + adjustment layer 3) |
|---|---|---|---|---|---|
| BI emission region (MQW) | $In_{0.52}Al_{0.48}As$ | 3.8 | 3.8 | 3.8 | 3.8 |
| | $In_{0.53}Ga_{0.47}As$ | 2.1(W4) | 2.1(W4) | 2.1(W4) | 2.1(W4) |
| | $In_{0.52}Al_{0.48}As$ | 0.7 | 0.7 | 0.7 | 0.7 |
| | $In_{0.53}Ga_{0.47}As$ | 6.3(W1) | 6.4(W1) | 6.5(W1) | 6.6(W1) |
| | $In_{0.52}Al_{0.48}As$ | 1.2 | 1.2 | 1.2 | 1.2 |
| | $In_{0.53}Ga_{0.47}As$ | 5.1(W2) | 5.1(W2) | 5.1(W2) | 5.1(W2) |
| | $In_{0.52}Al_{0.48}As$ | 1.4 | 1.4 | 1.4 | 1.4 |
| | $In_{0.53}Ga_{0.47}As$ | 5.1(W3) | 5.1(W3) | 5.1(W3) | 5.1(W3) |
| BE electron injection region (M) | $In_{0.52}Al_{0.48}As$ | 1.9 | 1.9 | 1.9 | 1.9 |
| | $In_{0.53}Ga_{0.47}As$ | 3.9 | 3.9 | 3.9 | 3.9 |
| | $In_{0.52}Al_{0.48}As$ | 1.3 | 1.3 | 1.3 | 1.3 |
| | $In_{0.53}Ga_{0.47}As$ | 3.8 | 3.8 | 3.8 | 3.8 |
| | $In_{0.52}Al_{0.48}As$ | 1.2 | 1.2 | 1.2 | 1.2 |
| | $In_{0.53}Ga_{0.47}As$ | 4.2 | 4.2 | 4.2 | 4.2 |
| | $In_{0.52}Al_{0.48}As$ | 1.9 | 1.9 | 1.9 | 1.9 |
| | $In_{0.53}Ga_{0.47}As$ | 2.4 | 2.4 | 2.4 | 2.4 |
| | $In_{0.52}Al_{0.48}As$ | 2.3 | 2.3 | 2.3 | 2.3 |
| | $In_{0.53}Ga_{0.47}As$ | 2.8 | 2.8 | 2.8 | 2.8 |
| | $In_{0.52}Al_{0.48}As$ | 2.3 | 2.3 | 2.3 | 2.3 |
| | $In_{0.53}Ga_{0.47}As$ | 3.2 | 3.2 | 3.2 | 3.2 |
| | $In_{0.52}Al_{0.48}As$ | 3.0 | 3.0 | 3.0 | 3.0 |
| | $In_{0.53}Ga_{0.47}As$ | 2.5 | 2.5 | 2.5 | 2.5 |
| adjustment quantum well layer (T) | $In_{0.52}Al_{0.48}As$ |  | 3.0 | 3.0 | 3.0 |
| | $In_{0.53}Ga_{0.47}As$ |  | 2.5 | 2.5 | 2.5 |
| | $In_{0.52}Al_{0.48}As$ |  |  | 3.0 | 3.0 |
| | $In_{0.53}Ga_{0.47}As$ |  |  | 2.5 | 2.5 |
| | $In_{0.52}Al_{0.48}As$ |  |  |  | 3.0 |
| | $In_{0.53}Ga_{0.47}As$ |  |  |  | 2.5 |

The different energy difference (Lu–Ll) is different between two unit stacked bodies having different widths W1 of the first well layers. Therefore, an electron injection efficiency may be decreased and an optical output may be decreased. In the second embodiment, a transition energy level Lt1 lower than the mini-band level Lm is created continuously from the adjustment quantum well layer 90 of the upstream first unit stacked body 80 to the second quantum well layer 94 of the second unit stacked body adjacent to the downstream and having different emission wavelength.

In the case of a comparative example (structure A), the width W1 of the first well layer is 6.3 nm, and the comparative example does not include the adjustment quantum well layer. The example I of the second embodiment (structure B+adjustment layer 1) includes the adjustment quantum well layer 90 made of one pair of well layer/barrier layer. The example II (structure C+two pairs of well layer/barrier layer) includes the adjustment quantum well layer made of two pairs of well layer/barrier layer. The example III (structure D+three pairs of well layer/barrier layer) includes the adjustment quantum well layer made of three pairs of well layer/barrier layer.

Figure 4A:
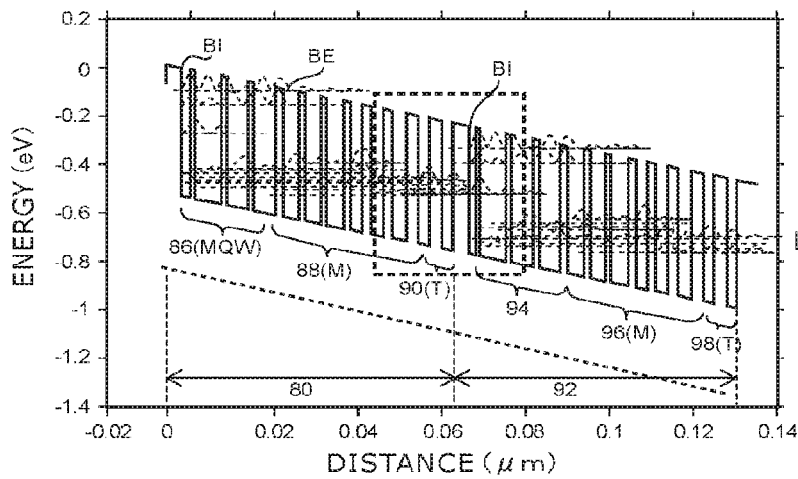
FIG. 4A is an energy band diagram of an example I of a second embodiment.
Figure 4B:
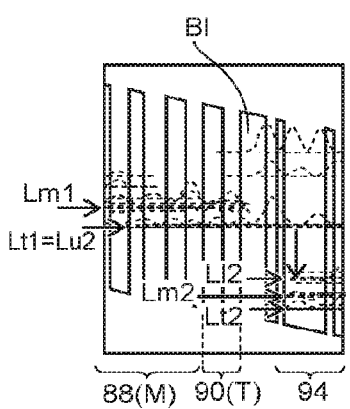
FIG. 4B is an enlarged view of the broken line region.
Figure 4C:
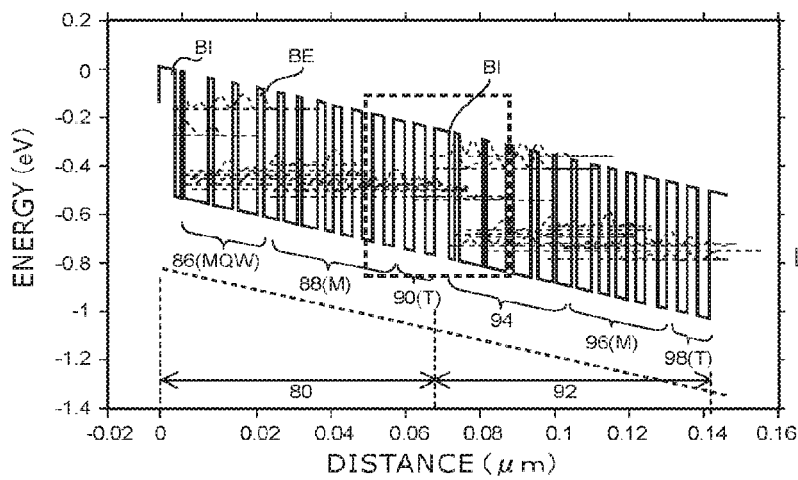
FIG. 4C shows an energy band diagram of an example II.
Figure 4D:
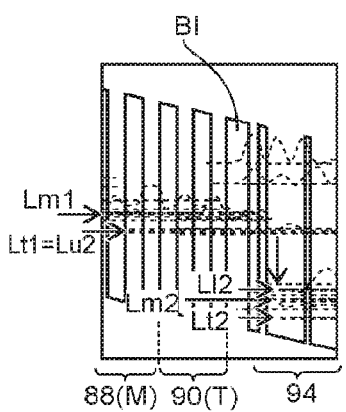
FIG. 4D is an enlarged view of the broken line region.
Figure 4E:
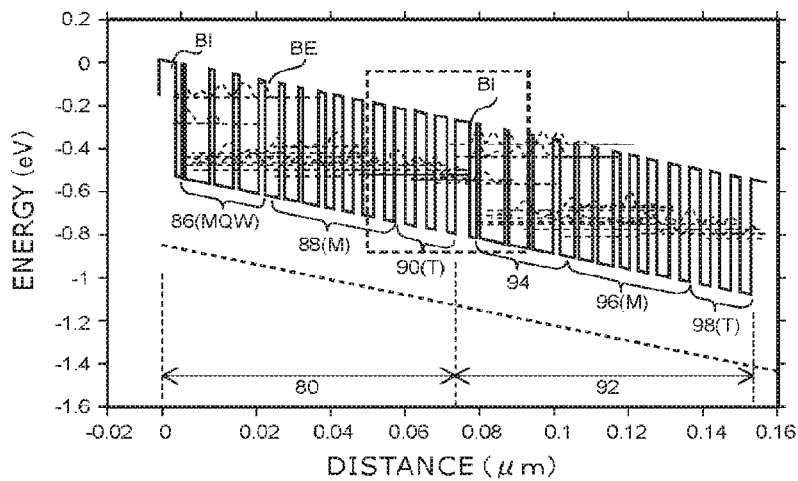
FIG. 4E shows an energy band diagram of an example 3.
Figure 4F:
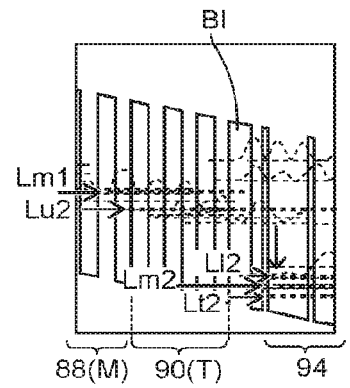
FIG. 4F is an enlarged view of the broken line region.

FIG. 4A is an energy band diagram of an example I of the second embodiment, FIG. 4B is an enlarged view of the broken line region, FIG. 4C shows an energy band diagram of an example II, FIG. 4D is an enlarged view of the broken line region, FIG. 4E shows an energy band diagram of an example 3, FIG. 4F is an enlarged view of the broken line region.

In the example I, the example II, the example III, the transition energy level Lt1 lower than the mini-band level Lm1 is created continuously from the adjustment quantum well layer 90 of the first unit stacked body 80 to the second emission region 94. Therefore, even if the unit stacked body having different constitution is set to have the cascade structure, the electron injection efficient can be held to be high.

Figure 5:
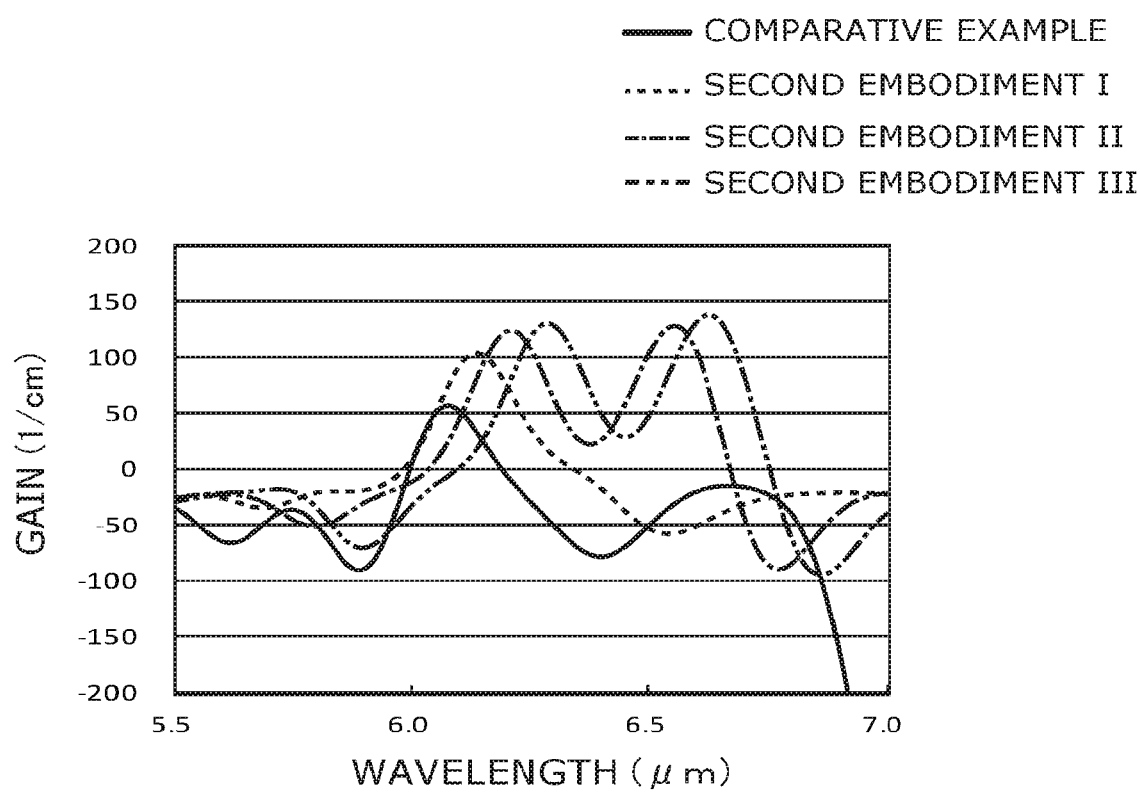
FIG. 5 shows a graph of a gain to an emission wavelength of the semiconductor laser device according to the second embodiment.

FIG. 5 shows a graph of a gain to an emission wavelength of the semiconductor laser device according to the second embodiment.

The injection regions of the example I, the example II, the example III of the second embodiment shown in (Table 1) have the adjustment quantum well layer 90 stacked with one, two, three layers of a pair of the well layer (thickness 2.5 nm) and the barrier layer (thickness 3 nm), respectively. In the second embodiment, the electron injection efficiency can be increased, and a gain and the optical output can be increased. Therefore, this makes it easy to widen the emission wavelength band. The constitution of the adjustment quantum well layer 90 is not limited thereto. Depending on the width W1 of the first well layer in the emission region cascade-connected on the downstream of the carrier, the width and the repeated periodicity of the well layer/barrier layer constituting the adjustment quantum well layer 90 can be determined. The cross section of the active layer 24 is able to be analyzed by TEM (Transmission Electron Microscopy).

For example, if the unit stacked body of the example I and the unit stacked body of the example III are alternately stacked, both gains are added and further wide gain band can be achieved. Since the transition energy levels Lt1, Lt2 are created across the two unit stacked bodies, the electron injection efficiency can be increased.

Figure 6A:
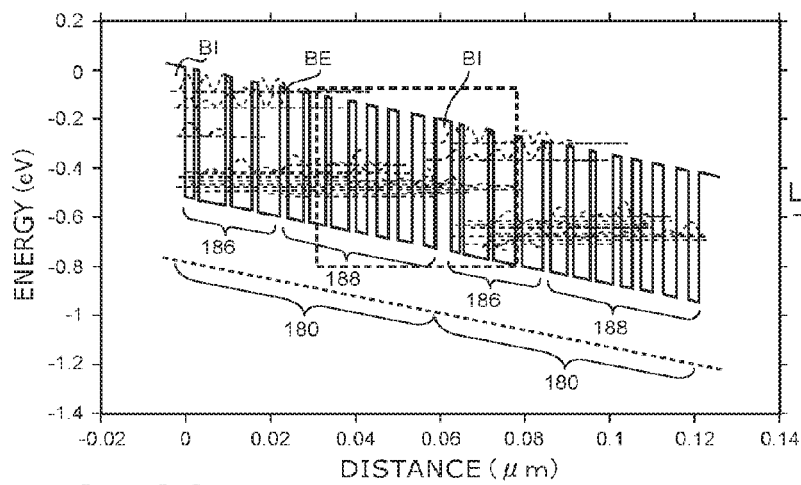
FIG. 6A is an energy band diagram according to a comparative example (W1=6.4 μm)
Figure 6B:
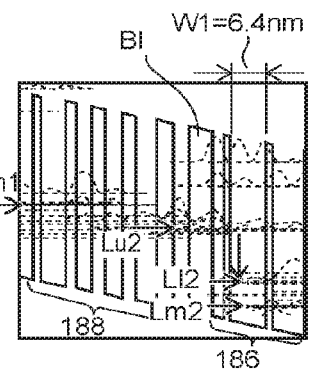
FIG. 6B is an enlarged view of the broken line region.
Figure 6C:
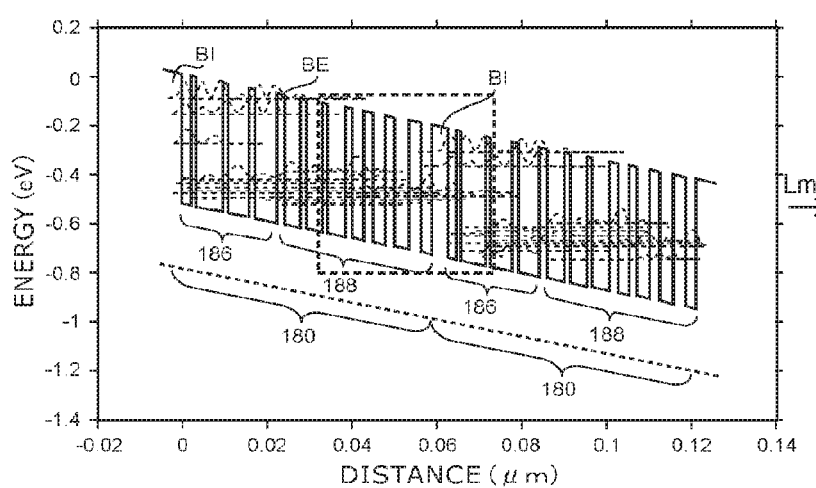
FIG. 6C is an energy band diagram according to a comparative example (W1=6.5 μm)
Figure 6D:
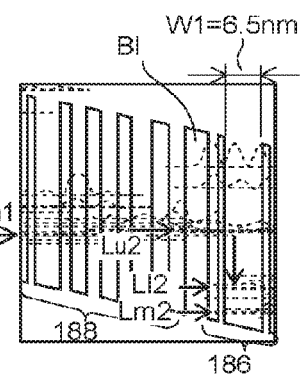
FIG. 6D is an enlarged view of the broken line region.
Figure 6E:
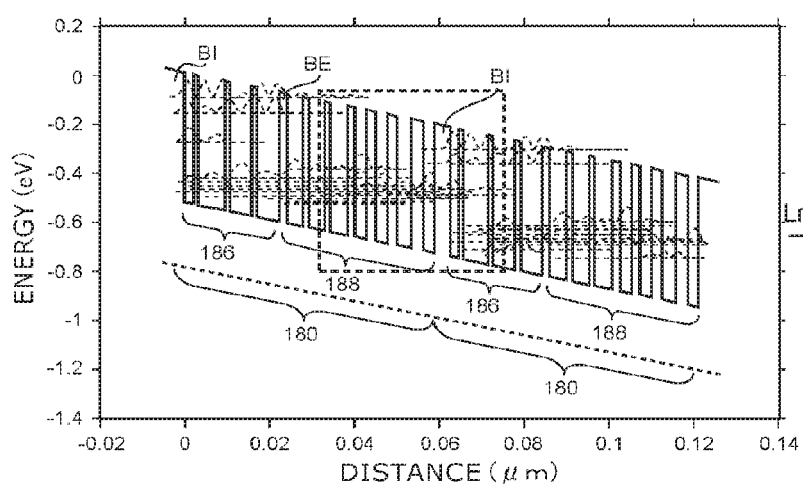
FIG. 6E is an energy band diagram according to a comparative example (W1=6.6 μm)
Figure 6F:
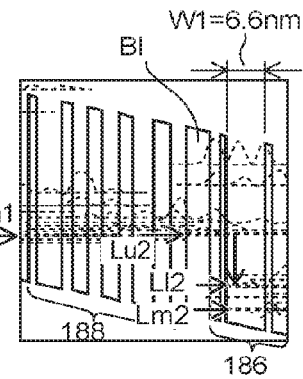
FIG. 6F is an enlarged view of the broken line region.

FIG. 6A is an energy band diagram according to the comparative example (W1=6.4 μm), FIG. 6B is an enlarged view of the broken line region, FIG. 6C is an energy band diagram according to the comparative example (W1=6.5 μm), FIG. 6D is an enlarged view of the broken line region, FIG. 6E is an energy band diagram according to the comparative example (W1=6.6 µm), FIG. 6F is an enlarged view of the broken line region.

The comparative example shows the energy band diagram of the unit stacked body not provided with the adjustment quantum well layer. In any of the cases of W1=6.4, 6.5, 6.6 µm, the mini-band levels Lm1 of the unit stacked body 180 are directly reproduced in the quantum well layer 186 of the next unit stacked body (same constitution 180) to form the high levels Lu2. That is, the transition energy level lower than the mini-band levels Lm1 making the electron injection easy does not exist near the interface. Therefore, the electron injection efficiency is likely to decrease at the interface of the unit stacked body and the optical output decreases.

In contrast, in the first and second embodiments, at least two unit stacked bodies having different well layer widths are stacked with periodicity. Therefore, a light emitting element capable of emitting infrared light over the wide wavelength band (including quantum cascade laser) is provided.

FIG. 7A is a configuration view of an exhalation diagnosis device according to the embodiment, FIG. 7B is a schematic view of an absorption spectrum of a plurality of gases, FIG. 7C is a view for describing a first adjustment mechanism and a second adjustment mechanism of a wavelength control unit.

The exhalation diagnosis device includes a quantum cascade laser 170 or the like, a wavelength control unit, a gas cell (corresponding to "chassis") 280, a detection unit 287, and a signal processing unit 288. The quantum cascade laser 170 and the wavelength control unit can be referred to as a light source unit 191.

The wavelength control unit includes the first adjustment mechanism shifting the wavelength of the infrared laser light or the like into an absorption spectrum of one kind of gas of a plurality kinds of gases included in exhalation of human being or the like, and a second adjustment mechanism shifting within the absorption spectrum of one kind of gas.

In the exhalation diagnosis device, the first adjustment mechanism includes a diffraction grating 171 or the like. The diffraction grating 171 is provided so as to cross an optical axis 162 of the quantum cascade laser 170, and constitutes an external resonator. As shown in FIG. 7(c), in exhalation BR including a plurality of gases, an incident angle of the infrared laser light is changed from β1 to β4 or the like depending on the spectrum of respective gases, and the wavelength of the infrared laser light is changed (coarse adjustment).

The diffraction grating 171 is rotationally controlled about an axis crossing the optical axis 162 by a stepping motor 199 and a controller 198 controlling it. An anti-reflection coating film AR is favorable to be provided on an end surface of the quantum cascade laser 70 on a side of the diffraction grating 171. Furthermore, if a partial reflection coating film PR is provided on an opposite side to the anti-reflection coating film AR, the external resonator can be constituted with the diffraction grating 171.

An absorption spectrum of a molecule is discrete, and in order to improve measurement accuracy, a wavelength is needed to meet an absorption peak accurately. In order to avoid absorption of carbon dioxide and water which are main components in the exhalation, and to measure absorption of a molecule to be measured, the wavelength is needed to be tuned in to the absorption peak accurately. However, the wavelengths of the absorption peak of a molecule and the light source may be influenced by measurement environment to shift. Therefore, fine-adjustment by the second adjustment mechanism is favorable.

As shown in FIG. 7C, the second adjustment mechanism does not rotate the diffraction grating 171 to be constant. Wavelength adjustment can be realized by changing an operating current $I_{LD}$ or duty of the quantum cascade laser 170, changing an operating temperature of the quantum cascade laser 170 by using a Peltier element 290 or the like, or changing an external resonator length by a piezoelectric element or the like. The second adjustment mechanism may change the operating temperature of the quantum cascade laser 170 by one of a chiller, a heater and a refrigerant or combination use. The refrigerant may be one of liquid nitrogen, water, ethanol water, and liquid helium.

As shown in FIG. 7B, for example, gas concentrations of acetone (a peak of absorption amount represented by a vertical axis is near 7.37 µm) and methane (a peak of absorption amount is near 7.7 µm) are set to be measured. Absorption spectra of different gases are greatly separated by, for example, generally 0.3 µm or the like. Therefore, in order to measure a plurality of gases in a short time (for example, one minute or the like), it is favorable to sweep quickly the wavelength of infrared laser light and to increase the shift range.

On the other hand, in the case where wavelength adjustment is performed in the absorption spectrum of one gas in the second adjustment mechanism, a shift range may be narrower than a wavelength range in the first adjustment mechanism. However, adjustment accuracy is required to be improved. That is, it is not easy to realize the first adjustment mechanism which is mainly used for coarse adjustment and the second mechanism which is mainly used for fine adjustment by using the same wavelength control mechanism.

A gas cell 280 includes an exhalation suction port 281, an exhalation exhaust port 282, an incident window 293 of the infrared laser light, and an emission window 284 of the infrared laser light. The laser light from the quantum cascade laser 170 has a divergence angle. For this reason, it is preferred to provide an optical system 272 for collimating between the quantum cascade laser 170 and the incident window 283. It is preferred to provide a light focusing system 286 between the emission window 284 and the detector 287.

The human exhalation BR includes nitrogen, oxygen, carbon dioxide, water or the like as a main component. Simultaneously, extremely small amount of different molecules of 1000 kinds or more are included. A change of small amount of gas serves as an index of disease. For this reason, when the small amount of gas G1 included in the exhalation is measured, early detection and prevention of the disease becomes possible. If the exhalation diagnosis device is used like this, the diagnosis can be made in a shorter time and more easily than performing a blood test.

For example, if acetone can be detected as the small amount of gas G1, diabetes or the like can be detected. In this case, detection sensitivity of the ppm degree using the infrared ray having a wavelength of 7 to 8 µm is necessary. If ammonia can be detected as the small amount gas, hepatitis can be detected. In this case, detection sensitivity of the ppm degree using the infrared ray having a wavelength of 10.3 µm is necessary. If ethanol and acetaldehyde can be detected as the small amount of gas, an amount of drinking can be measured.

If the emission wavelength range of the quantum cascade laser 170 is narrow, a plurality of quantum cascade lasers 170 and a plurality of external resonators corresponding to the respective quantum cascade lasers are necessary in order to generate the infrared laser light with the wide wavelength range. For this reason, a device is increased in size. In contrast, the quantum cascade laser according to the embodiment has a wide emission wavelength band. Therefore, the infrared laser light with the wide wavelength range can be emitted in one quantum cascade laser, and the device can be downsized.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

The invention claimed is:

1. A semiconductor laser device comprising:
a plurality of first unit stacked bodies having an emission region including a first quantum well layer and capable of emitting a first infrared light by an intersubband transition, an electron injection region capable of transporting an electron relaxed to a mini-band level in the emission region to a downstream unit stacked body, and an adjustment quantum well layer on a downstream of the electron injection region; and
a plurality of second unit stacked bodies having an emission region including a second quantum well layer and capable of emitting a second infrared light by an intersubband transition, an electron injection region capable of transporting an electron relaxed to a mini-band level in the emission region of the second quantum well layer to a downstream unit stacked body, and an adjustment quantum well layer on a downstream of the electron injection region, the second quantum well layer having at least one well width different from a well width of the first quantum well layer,
a first unit stacked body and a second unit stacked body being stacked with spatial periodicity, and
an adjustment quantum well layer of a unit stacked body on an upstream creating continuously a transition energy level lower than a mini-band level in an electron injection region on an upstream to an emission region of a unit stacked body adjacent on a downstream at an interface where a first unit stacked body and a second unit stacked body are stacked.

2. The semiconductor laser device according to claim 1, wherein the adjustment quantum well layer of at least one of the plurality of first unit stacked bodies and the plurality of second unit stacked bodies includes a plurality of pairs of a well layer and a barrier layer having same structure.

3. The semiconductor laser device according to claim 2, wherein
an electron injection region adjacent to an upstream of the adjustment quantum well layer of the at least one includes a plurality of quantum well layers, and
a width of the well layer and a width of the barrier layer of the adjustment quantum well layer of the at least one are same as a width of a well layer and a width of a barrier layer forming adjacent quantum well layer of the plurality of quantum well layers respectively.

4. A semiconductor laser device comprising:
a plurality of first unit stacked bodies having an emission region including a first quantum well layer and capable of emitting a first infrared light by an intersubband transition, an electron injection region capable of transporting an electron relaxed to a mini-band level in the emission region to a downstream unit stacked body, an injection barrier layer injecting an electron into the first quantum well layer and an extracting barrier layer extracting an electron from the first quantum well layer, and
a plurality of second unit stacked bodies having an emission region including a second quantum well layer and capable of emitting a second infrared light by an intersubband transition, an electron injection region capable of transporting an electron relaxed to a mini-band level in the emission region of the second quantum well layer to a downstream unit stacked body, an injection barrier layer injecting an electron into the second quantum well layer and an extracting barrier layer extracting an electron from the second quantum well layer, the second quantum well layer having at least one well width different from a well width of the first quantum well layer,
a first unit stacked body and a second unit stacked body being stacked with spatial periodicity.

5. A semiconductor laser device comprising:
a plurality of first unit stacked bodies having an emission region including a first quantum well layer and capable of emitting a first infrared light by an intersubband transition, an electron injection region capable of transporting an electron relaxed to a mini-band level in the emission region to a downstream unit stacked body, and an adjustment quantum well layer on a downstream of the electron injection region,
a plurality of second unit stacked bodies having an emission region including a second quantum well layer and capable of emitting a second infrared light by an intersubband transition, an electron injection region capable of transporting an electron relaxed to a mini-band level in the emission region of the second quantum well layer to a downstream unit stacked body, and an adjustment quantum well layer on a downstream of the electron injection region, the second quantum well layer having at least one well width different from a well width of the first quantum well layer,
a first unit stacked body and a second unit stacked body being stacked with spatial periodicity
a well width of a well layer determining the intersubband transition in the first quantum well layer being different from a well width of a well layer determining the intersubband transition in the second quantum well layer, and
an adjustment quantum well layer of a unit stacked body on an upstream creates continuously a transition energy level lower than a mini-band level in an electron injection region on an upstream to an emission region of a unit stacked body adjacent on a downstream at an interface where a first unit stacked body and a second unit stacked body are stacked.

6. The semiconductor laser device according to claim 5, wherein the adjustment quantum well layer of at least one of the plurality of first unit stacked bodies and the plurality of second unit stacked bodies includes a plurality of pairs of a well layer and a barrier layer having same structure.

7. The semiconductor laser device according to claim 6, wherein
an electron injection region adjacent to an upstream of the adjustment quantum well layer of the at least one includes a plurality of quantum well layers, and a width of the well layer and a width of the barrier layer of the adjustment quantum well layer of the at least one are same as a width of a well layer and a width of a barrier layer forming adjacent quantum well layer of the plurality of quantum well layers respectively.

8. A semiconductor laser device comprising:

a plurality of first unit stacked bodies having an emission region including a first quantum well layer and capable of emitting a first infrared light by an intersubband transition, and an electron injection region capable of transporting an electron relaxed to a mini-band level in the emission region to a downstream unit stacked body;

a plurality of second unit stacked bodies having an emission region including a second quantum well layer and capable of emitting a second infrared light by an intersubband transition, and an electron injection region capable of transporting an electron relaxed to a mini-band level in the emission region of the second quantum well layer to a downstream unit stacked body, the second quantum well layer having at least one well width different from a well width of the first quantum well layer, and a plurality of third unit stacked bodies having an emission region including a third quantum well layer and capable of emitting a third infrared light by an intersubband transition, and an electron injection region capable of transporting an electron relaxed to a mini-band level in the emission region of the third quantum well layer to a downstream unit stacked body, the third quantum well layer having at least one well width different from the well width of the first quantum well layer and the well width of the second quantum well layer, a first unit stacked body, a second stacked body and the third unit stacked body being stacked with spatial periodicity.

9. The semiconductor laser device according to claim 8, wherein all of a well width of a well layer determining the intersubband transition in the first quantum well layer, a well width of a well layer determining the intersubband transition in the second quantum well layer, and a well width of a well layer determining the intersubband transition in the third quantum well layer are different.

10. The semiconductor laser device according to claim 8, wherein the plurality of first unit stacked bodies include an adjustment quantum well layer on a downstream of the electron injection region, the plurality of second unit stacked bodies include an adjustment quantum well layer on a downstream of the electron injection region, the plurality of third unit stacked bodies include an adjustment quantum well layer on a downstream of the electron injection region, and at an interface where two of a first unit stacked body, a second unit stacked body and a third unit stacked body are stacked, an adjustment quantum well layer of a unit stacked body on an upstream creates continuously a transition energy level lower than a mini-band level in an electron injection region on an upstream to an emission region of a unit stacked body adjacent on a downstream.

* * * * *